(12) United States Patent
Grascha et al.

(10) Patent No.: US 8,362,077 B2
(45) Date of Patent: Jan. 29, 2013

(54) CHEMICAL COMPOSITIONS FOR SKIN CARE EMULSIONS AND HEAVY DUTY HAND CLEANSERS

(75) Inventors: Pierre Bruno Grascha, Cormontreuil (FR); Mylene Battut, La Norville (FR)

(73) Assignee: Pibed Limited, Belper, Derbyshire (GB)

( * ) Notice: Subject to any disclaimer, the term of this patent is extended or adjusted under 35 U.S.C. 154(b) by 4 days.

(21) Appl. No.: 12/222,806

(22) Filed: Aug. 15, 2008

(65) Prior Publication Data

US 2010/0041774 A1 Feb. 18, 2010

(51) Int. Cl.
| | | |
|---|---|---|
| A61K 8/37 | (2006.01) | |
| A61K 8/34 | (2006.01) | |
| A61K 31/45 | (2006.01) | |
| A61K 31/23 | (2006.01) | |
| A01N 37/02 | (2006.01) | |
| A01N 31/02 | (2006.01) | |
| A01N 31/04 | (2006.01) | |

(52) U.S. Cl. ......... 514/552; 424/401; 514/730; 514/739
(58) Field of Classification Search ........................ None
See application file for complete search history.

(56) References Cited

U.S. PATENT DOCUMENTS

| | | | |
|---|---|---|---|
| 4,921,694 A * | 5/1990 | Hoppe et al. ..................... | 424/65 |
| 5,098,694 A | 3/1992 | Komp et al. | |
| 5,318,726 A * | 6/1994 | Rossmaier et al. ........... | 510/361 |
| 5,460,802 A | 10/1995 | Asami et al. | |
| 7,067,140 B2 * | 6/2006 | Koike et al. .................... | 424/401 |
| 7,252,830 B2 * | 8/2007 | Novikov et al. ............... | 424/401 |
| 2004/0228888 A1 | 11/2004 | Kohlhase et al. | |
| 2006/0008434 A1 * | 1/2006 | Knopf et al. ..................... | 424/65 |
| 2006/0153792 A1 * | 7/2006 | Arnaud et al. .............. | 424/70.16 |
| 2007/0265352 A1 | 11/2007 | Roeding et al. | |

FOREIGN PATENT DOCUMENTS

| | | | |
|---|---|---|---|
| DE | 19850359 A1 * | 5/2000 | |
| EP | 0 420 630 | 4/1991 | |
| GB | 2 345 636 | 7/2000 | |
| WO | WO 91/09106 | * | 6/1991 |
| WO | WO 00/67705 | * | 11/2000 |
| WO | WO-0124769 | * | 4/2001 |
| WO | 02/19981 | | 3/2002 |
| WO | 2006/096239 | | 9/2006 |

OTHER PUBLICATIONS

Inoue et al. (FEMS Microbiology Letters 2004, 237, 325-331).*
Kubo et al. (Bioorganic & Medicinal Chemistry 1995, 3, 873-880).*
Ruzin et al. (Journal of Bacteriology 2000, 182, 2668-2671).*
Antimicrob. Agents Chemother. 2003, 47(10):3357.*
Brehm-Stecher et al. "Sensitization of *Staphylococcus aureus* and *Escherichia coli* to antibiotics by the sesquiterpenoids nerolidol, farnesol, bisabolol, and apritone." Antimicrobial Agents and Chemotherapy. American Society for Microbiology. vol. 47, No. 10, pp. 3357-3360. Oct. 1, 2003.
Liu et al. "Inhibition of protease production of various bacteria by ammonium salts: its effect on toxin production and virulence." Journal of Bacteriology. vol. 99, No. 2, pp. 406-413. Aug. 1969.
Comes et al. "Addition of fumaric acid and sodium benzoate as an alternative method to achieve a 5-log reduction of *Escherichia coli* 0157:H7 populations in apple cider." Journal of Food Protection. International Association for Food Protection. vol. 65, No. 3, pp. 476-483. Mar. 1, 2002.
Lee et al. "Antifungal effect of eugenol and nerolidol against *Microsporum gypseum* in a guinea pig model." Medicinal & Aromatic Plants Abstracts. Scientific Publishers. vol. 29, No. 6, p. 187. Dec. 1, 2007.
Inoue et al. "The antibacterial effects of terpene alcohols on *Staphylococcus aureus* and their mode of action." FEMS Microbiology Letters. vol. 237, pp. 325-331. Jul. 8, 2004.
Siegert, Wolfgang. "Can new biodegradable complexing agents replace tetrasodium edta to boost preservatives?" SOFW Journal. No. 134, pp. 22-26. Jan. 2008.

* cited by examiner

*Primary Examiner* — James H Alstrum Acevedo
*Assistant Examiner* — Jessica Kassa

(57) ABSTRACT

The present invention provides preservative compositions suitable for replacing, partially or in totality, conventional preservatives in skin care emulsions and heavy duty hand cleansers comprised of alternative molecular compounds than found in conventional preservative formulations. The preservative formulation for skin care formulations includes a fatty acid and/or ester of fatty acid present in a concentration from about 0.01 wt./wt. % to about 90 wt./wt. % of the formulation, one or more alcohols in a concentration from about 0.01 to about 60 wt./wt. % of the formulation, and a chelating agent present in a concentration from about 0.01 to about 20 wt./wt. % of the blend.

32 Claims, No Drawings

CHEMICAL COMPOSITIONS FOR SKIN CARE EMULSIONS AND HEAVY DUTY HAND CLEANSERS

FIELD OF THE INVENTION

The present invention relates to a chemical composition designed to protect skin care emulsions and heavy duty hand cleanser products from microbial degradation, with or without using conventional preservatives.

BACKGROUND TO THE INVENTION

The term "preservative" is generally defined as an industry-recognized ingredient the purpose of which is to prevent microbial growth in consumer products such as a cosmetics and food. Some preservatives (formaldehyde releasers, isothiazolinones . . . ) are known to cause a host of skin irritations, such as dryness, redness and even breakouts. The only goal of preservatives is to extend the life of a product beyond what it would be naturally in the absence of the preservative. As mentioned, the most significant concern with respect to preservatives in personal skin products, cosmetics, soaps etc. would be skin irritations that can vary from mild to very severe. Preservatives can cause many skin disorders and allergies from eczema to rosacea to blemishes.

Some natural or synthetic materials are not regulated as preservatives, yet when used for their beneficial effect on the skin, may coincidentally have a positive effect on the total preservative requirement of the formulation. In view of increasing pressure from consumers and cosmetic regulation bodies alike, and because of bad press concerning the presence and use of more and more chemical preservatives (especially formaldehyde releasers and parabens), it would be advantageous to formulate preservative-free products that do not rely on, or incorporate presently regulated as preservatives.

It would therefore be advantageous to provide preservative-free formulations for protecting skin care emulsions and heavy duty hand cleanser products from microbial degradation.

SUMMARY OF THE INVENTION

The inventors have discovered preservative compositions using a natural biochemical process, involving alternative molecular compounds than found in known commercial preservative formulations.

The present invention provides preservative compositions suitable for replacing, partially or in totality, conventional preservatives in skin care emulsions and heavy duty hand cleansers.

The present invention provides a preservative formulation for skin care products, comprising constituents including:
  a) glyceril laurate present in a concentration from about 0.01 wt./wt. % to about 90 wt./wt. % of the formulation;
  b) at least one alcohol selected from the group consisting of nerolidol, phenyl hexanol, and any combination thereof present a concentration from about 0.01 to about 60 wt./wt. % of the formulation; and
  c) at least one chelating agent present in a concentration from about 0.01 to about 20 wt./wt. % of the formulation.

An embodiment of the invention includes a preservative formulation for skin care products, comprising constituents including:
  a) glyceryl laurate present in a concentration from about 55 wt./wt. % to about 90wt./wt. % of the formulation;
  b) at least one alcohol selected from the group consisting of nerolidol, phenyl hexanol, and any combination thereof present in a concentration from about 0.01 to about 30 wt./wt. %, wherein, if present, nerolidol is present in a concentration of up to about 11 wt./wt. %, and if present, phenyl hexanol is present in a concentration of up to about 30 wt./wt. % of the formulation; and
  c) at least one chelating agent present in a concentration from about 0.01 to about 20 wt./wt. % of the formulation.

Another embodiment of the invention is a preservative formulation for a personal hygiene product, comprising constituents including:
  a) glyceryl laurate present in a concentration from about 55 wt./wt. % to about 87 wt./wt. % of the formulation;
  b) at least one alcohol selected from a group consisting of nerolidol, phenyl hexanol, and any combination thereof wherein if present, nerolidol is present in a concentration of from about 3 to about 11 wt./wt. %, and wherein if present, phenyl hexanol is present in a concentration of from about 20 to about 30 wt./wt. %; and
  c) at least one chelating agent present in a concentration from about 0.01 to about 20 wt./wt. % of the formulation; and wherein
  d) the preservative formulation of constituent a), b) and c) being incorporated into the personal hygiene product to form a preserved personal hygiene product, with the preservative formulation being present in a concentration range from about 0.1 to about 10 wt./wt. % of the preserved personal hygiene product.

In an aspect, a formulation of the invention is one in which sodium iminodisuccinate is present in a range from about 3.0% wt./wt. to about 11% wt./wt., phenyl hexanol is present in a range from about 20% wt./wt. to about 30% wt./wt., nerolidol is present in a range from about 3% wt./wt. to about 7% wt./wt., and glyceryl laurate is present in a range from about 55% wt./wt. to about 70% wt./wt.

In another aspect, a formulation of the invention is one in which sodium iminodisuccinate is present in a range from about 4.0% wt./wt. to about 16% wt./wt., nerolidol is present in a range from about 4% wt./wt. to about 11% wt./wt., and glyceryl laurate is present in a range from about 80% wt./wt. to about 87% wt./wt.

The present chemical compositions have exhibited no known potential toxicity or ecotoxicity, are not regulated as preservatives, having nothing in common with existing preservatives on the market, and have demonstrated efficacy for bacteriostatic and fungistatic properties.

DETAILED DESCRIPTION OF THE INVENTION

Generally speaking, the embodiments described herein are directed to chemical formulations as preservatives for skin care emulsions and heavy duty hand cleansers comprised of alternative molecular compounds than found in conventional preservatives. As required, embodiments of the present invention are disclosed herein. However, the disclosed embodiments are merely exemplary, and it should be understood that the invention may be embodied in many various and alternative forms. The figures are not to scale and some features may be exaggerated or minimized to show details of particular elements while related elements may have been eliminated to prevent obscuring novel aspects. Therefore, specific structural and functional details disclosed herein are not to be interpreted as limiting but merely as a basis for the claims and as a representative basis for teaching one skilled in the art to variously employ the present invention. For purposes of teaching and not limitation, chemical formulations as preservatives for skin care emulsions and heavy duty hand cleansers comprised of alternative molecular compounds than in known preservative formulations are disclosed.

As used herein, the terms "about", and "approximately" when used in conjunction with ranges of dimensions, concentrations, temperatures or other physical properties or characteristics is meant to cover slight variations that may exist in the upper and lower limits of the ranges of properties/characteristics.

Embodiments of the preservative composition disclosed herein include at least one fatty acid and/or ester of the fatty acid such as the $C_8$ to $C_{22}$-alkyl or -aryl fatty acids or esters thereof. Preferred embodiments are particularly $C_{10}$ to $C_{12}$ fatty acids or esters thereof, and even more preferred is $C_{12}$ fatty acid or ester thereof, and mixtures thereof. A preferred fatty acid is lauric acid. A preferred ester of the fatty acid is glyceryl laurate.

The alcohol may be any one of $C_2$ to $C_{22}$-alkyl alcohols, aryl (aromatic) alcohols, aromatic alcohols, terpenic alcohols, any of their isomers, and mixtures thereof. Preferred alcohols are phenyl alcohol and/or sesquiterpenic alcohol or combinations thereof. Even more preferred alcohols are phenyl hexanol and/or nerolidol (3,7,11-trimethyl-1,6,10-dodecatrien-3-ol), and any mixture thereof.

The chelating agent may be any one of biodegradable chelating agents such as gluconic acid, its sodium salts, iminodisuccinic acid, its sodium salts, and any mixtures thereof. The biodegradable chelating agent is preferably tetrasodium 3-hydroxy-2,2'-iminodisuccinate.

The preservative chemical formulations disclosed herein are formulated to effectively replace conventional preservatives, to reduce the risk of dermal toxicity.

The preservative chemical formulations disclosed herein may be incorporated into surfactant-containing hygiene products or emulsions, gels and lotions for skin care purposes having potential antimicrobial activity, in a concentration range from 0.1 to 80 wt./wt. % of the finished products, and preferably from about 1.00% to about 5.00% wt./wt.

The final pH of the preserved formulations is preferably from about pH 3 to about 9, more preferably from about pH 5 to about pH 8.

Mode of Operation

Studies by the inventors using certain preferred constituents have been performed. The action of these preferred constituents and their mode of operation are discussed below, however it will be understood by those skilled in the art that the present invention is not to be limited by any theory. Studies by the inventors have shown that the preservative chemical formulations disclosed herein are able to inhibit the growth of Gram negative bacteria, Gram positive bacteria, yeasts and moulds, all potential contaminants of water-based cosmetic and pharmaceutical products. While not meaning to be limited by any theory, the inventors believe that the mode of action on bacteria by the present formulations is mainly based on the inhibition of energy releasing biochemical reactions. On yeast and moulds, the formulations are believed to disrupt the cell-wall. All involved ingredients are chosen to synergistically act on various cell-targets (metabolism, cell-wall, cell-membrane, cytoplasma, DNA, etc. . . . ) through chemical and physical modes of action.

In order to check the efficacy and effectiveness of the present formulations, a selected blend (sodium iminodisuccinate 11.40%, glyceryl laurate 57.10%, phenyl hexanol 28.60% and nerolidol 2.90%) was challenge-tested against four test-microorganisms, at a final concentration of 4.00% in water, and according to the United States Pharmacopeia (USP) test-method.

The following table shows the obtained results (expressed in terms of logarithm reductions). The blend passed the criteria for all test-microorganisms.

| Test-microorganisms | USP (criteria) | Test-results |
|---|---|---|
| S. aureus (ATCC 6538) | Day 14 ≧ 2 log | >4 log |
| P. aeruginosa (ATCC 9027) | Day 14 ≧ 2 log | >4 log |
| C. albicans (ATCC 10231) | Day 28 = no increase in count | 0.20 log |
| A. niger (ATCC 16404) | Day 28 = no increase in count | 1.27 log |

Another test was conducted to determine the Minimum Inhibitory Concentration (from 1 to 4% w/w) of the same blend. The same test-microorganisms from the original ATCC cultures were grown and maintained in the laboratory according to the AFNOR EN12353 standard method.

Time and temperature of incubation were:
  24 h at 36+/−1° C. for bacteria
  48 h at 30+/−1° C. for yeasts and molds Culture media were:
  TSA (Tryptic Soy Agar) for bacteria
  Sabouraud agar without chloramphenicol for yeasts and molds The following table shows the obtained results (expressed in terms of number of Unit Forming Colonies—UFC). In the test conditions, the blend may be considered to be bacteriostatic and fungistatic at 4% w/w for all test-microorganisms.

| Test-microorganisms | Initial count | UFC at 1% | at 2% | at 3% | at 4% |
|---|---|---|---|---|---|
| S. aureus (ATCC 6538) | $1.7 \times 10^5$ | <1 | <1 | <1 | <1 |
| P. aeruginosa (ATCC 9027) | $2.2 \times 10^5$ | <1 | <1 | <1 | <1 |
| C. albicans (ATCC 10231) | $2.7 \times 10^5$ | <1 | <1 | <1 | <1 |
| A. niger (ATCC 16404) | $2.1 \times 10^5$ | $1.9 \times 10^5$ | $1.7 \times 10^5$ | $7.5 \times 10^4$ | $1.0 \times 10^3$ |

The unique composition of human breast milk fat includes the fatty acids, lauric acid and capric acid, which have potent antimicrobial properties. These fatty acids offer the nursing infant protection from viruses such as herpes and HIV, protozoa such as *Giardia, Lamblia*, and bacteria such as *Chlamydia* and *Helicobacter*.

Lauric acid is one of the most effective fatty acids (easily extracted from coconut oil); it is particularly effective on Gram positive bacteria but the glycerol ester of lauric acid (glyceryl laurate) is more biologically active than lauric acid. Due to its affinity for lipophilic substrates, its biocidal mode of action should be based on cell-membrane disruption.

Sodium Iminodisuccinaate

Sodium Iminodisuccinaate is a safe and biodegradable cosmetic chelating agent. Bacteria require metal ions to satisfy the specific requirements of metal-enzyme and cell-wall structural components. Chelators are able to increase the permeability of the bacterial cell wall by sequestering the necessary metals ($Fe^{2+}$ in particular). They also can capture the metal ions ($Mg^{2+}$ in particular) acting as cofactors for the DNA synthesis and in the LipoPolySaccharide's cohesion. Chelators are known to improve the antimicrobial activity of biocidal molecules.

Phenyl Hexanol

Aromatic alcohols are used in a great number of alternative preservatives. Phenyl ethanol is the most widely used but it has strong 'flowery' smell; a chemical structure analogue such as phenyl hexanol is a good alternative and has almost no smell.

Nerolidol

A natural sesquiterpene with bactericidal and fungicidal properties. A study consisting of evaluating the antibacterial effects of three terpene-alcohols (farnesol, nerolidol and plaunotol) on *Staphylococcus aureus*, focusing on the leakage of K+ ions and toxicity over time, suggested that the terpene alcohols may act on cell membranes. The antibacterial activity reflected the initial rate of leakage of K+ ions, suggesting that damage to cell membranes might be one of the major modes of action of these terpene alcohols. The results also demonstrated that the initial rate of leakage and the amount of leaked K+ ions are useful as indices of the antibacterial activities of hydrophobic compounds, see Yoshihiro Inouea, Akiko Shiraishia, Toshiko Hadaa, Kazuma Hirosea, Hajime Hamashimaa, Jingoro Shimada; "The antibacterial effects of terpene alcohols on *Staphylococcus aureus* and their mode of action", FEMS microbiology letters (FEMS microbiol. lett.) 2004, vol. 237, no 2, pp. 325-331.

In another study, sesquiterpenoids nerolidol, farnesol, bisabolol, and apritone were investigated for their abilities to enhance bacterial permeability and susceptibility to exogenous antimicrobial compounds. Initially, it was observed by flow cytometry that these sesquiterpenoids promoted the intracellular accumulation of the membrane-impermeant nucleic acid stain ethidium bromide by live cells of *Lactobacillus fermentum*, suggesting that enhanced permeability resulted from disruption of the cytoplasmic membrane. The ability of these sesquiterpenoids to increase bacterial susceptibility to a number of clinically important antibiotics was then investigated. In disk diffusion assays, treatment with low concentrations (0.5 to 2 mM) of nerolidol, bisabolol, or apritone enhanced the susceptibility of *Staphylococcus aureus* to ciprofloxacin, clindamycin, erythromycin, gentamicin, tetracycline, and vancomycin. Nerolidol and farnesol also sensitized *Escherichia coli* to polymyxin B, see Byron F. Brehm-Stecher1 and Eric A. Johnson Sensitization of *S. aureus* and *E. coli* to Antibiotics by the Sesquiterpenoids Nerolidol, Farnesol, Bisabolol, and Apritone Antimicrob Agents Chemother. October 2003; 47(10): 3357-3360.

Another study allowed to elucidate the antifungal activities of eugenol and nerolidol isolated from Japanese cypress oil in a guinea pig model infected by *Microsporum gypseum* (*M. gypseum*). A minimal inhibitory concentration (MIC), skin lesion scoring, hair culture and histopathologic examination of skin tissues were performed to evaluate the antifungal effect of these oils. The MICs of eugenol, nerolidol and econazole (positive control) were 0.01-0.03% and 0.5-2% and 4-16 µg/ml, respectively. Based on these MICs, eugenol and nerolidol were adjusted to 10% concentration with a base of Vaseline® petroleum jelly and were applied topically to the skin lesion infected with *M. gypseum* daily for 3 weeks. Both eugenol and nerolidol were clinically effective at improving the lesion during the first week of application, as determined by skin lesion scoring. Nerolidol improved the skin lesions infected by *M. gypseum*, but eugenol did not, as determined in the hair culture test. Histopathologic examination revealed that the eugenol- and nerolidol-treated groups had a lower degree of hyperkeratosis and inflammatory cell infiltration than the positive control. Taken together, these results suggest that eugenol and nerolidol could apply supplementary antifungal agents, see Sook-Jin Lee[1], Je-Ik Han[1], Geun-Shik Lee[2], Mi-Jin Park[3], In-Gyu Choi[3], Ki-Jeong Na[1] and Eui-Bae Jeung[2] Antifungal Effect of Eugenol and Nerolidol against *Microsporum gypseum* in a Guinea Pig Model, Biological & Pharmaceutical Bulletin, Vol. 30 (2007), No. 1 184.

The present invention will now be illustrated using the following non-limiting example formulations.

EXAMPLE 1

| Chemical Names | % w/w |
| --- | --- |
| GLYCERYL LAURATE | 57.00 |
| PHENYL HEXANOL | 29.00 |
| NEROLIDOL | 3.00 |
| SODIUM IMINODISUCCINATE | 11.00 |

The formulation of example 1 is useful for use in skin care emulsions and heavy duty hand cleanser products in a range from about 1 to about 5% wt./wt. in finished products.

EXAMPLE 2

| Chemical Names | % w/w |
| --- | --- |
| GLYCERYL LAURATE | 70.00 |
| PHENYL HEXANOL | 20.00 |
| NEROLIDOL | 6.00 |
| SODIUM IMINODISUCCINATE | 4.00 |

EXAMPLE 3

| Chemical Names | % w/w |
| --- | --- |
| GLYCERYL LAURATE | 57.00 |
| PHENYL HEXANOL | 29.00 |
| NEROLIDOL | 3.00 |
| SODIUM IMINODISUCCINATE | 11.00 |

EXAMPLE 4

| Chemical Names | % w/w |
| --- | --- |
| GLYCERYL LAURATE | 85.00 |
| NEROLIDOL | 11.00 |
| SODIUM IMINODISUCCINATE | 4.00 |

EXAMPLE 5

| Chemical Names | % w/w |
|---|---|
| GLYCERYL LAURATE | 87.00 |
| NEROLIDOL | 7.00 |
| SODIUM IMINODISUCCINATE | 6.00 |

EXAMPLE 6

| Chemical Names | % w/w |
|---|---|
| GLYCERYL LAURATE | 87.00 |
| NEROLIDOL | 4.00 |
| SODIUM IMINODISUCCINATE | 9.00 |

EXAMPLE 7

| Chemical Names | % w/w |
|---|---|
| GLYCERYL LAURATE | 80.00 |
| NEROLIDOL | 4.00 |
| SODIUM IMINODISUCCINATE | 16.00 |

The above blends are preferably incorporated into skin care and hygiene products in a concentration range from about 0.1 to about 80 wt./wt. % of the finished products.

As used herein, the terms "comprises", "comprising", "includes" and "including" are to be construed as being inclusive and open ended, and not exclusive. Specifically, when used in this specification including claims, the terms "comprises", "comprising", "includes" and "including" and variations thereof mean the specified features, steps or components are included. These terms are not to be interpreted to exclude the presence of other features, steps or components.

The foregoing description of the preferred embodiments of the invention has been presented to illustrate the principles of the invention and not to limit the invention to the particular embodiment illustrated. It is intended that the scope of the invention be defined by all of the embodiments encompassed within the following claims and their equivalents.

Therefore what is claimed is:

1. A preservative formulation for skin care products, comprising constituents including:
   a) glyceryl laurate present in a concentration from about 55 wt./wt. % to about 90 wt./wt. % of the formulation;
   b) at least one alcohol selected from the group consisting of nerolidol, phenyl hexanol, and any combination thereof present in a concentration from about 0.01 to about 30 wt./wt. %, wherein, if present, nerolidol is present in a concentration of up to about 11 wt./wt. %, and if present, phenyl hexanol is present in a concentration of up to about 30 wt./wt. % of the formulation; and
   c) at least one chelating agent present in a concentration from about 0.01 to about 20 wt./wt. % of the formulation.

2. The formulation according to claim 1 including at least one fatty acid being one of $C_8$ to $C_{22}$ alkyl fatty acids, $C_8$ to $C_{22}$ aryl fatty acids, and any combination thereof.

3. The formulation according to claim 1 including at least one fatty acid being one of $C_{10}$ to $C_{12}$ alkyl fatty acids, $C_{10}$ to $C_{12}$ aryl fatty acids, and any combination thereof.

4. The formulation according to claim 1 including lauric acid.

5. The formulation according to claim 1 wherein said at least one alcohol is phenyl hexanol.

6. The formulation according to claim 1 wherein said at least one alcohol is nerolidol (3,7,11-trimethyl-1,6,10-dodecatrien-3-ol).

7. The formulation according to claim 1 wherein said at least one chelating agent is selected from the group consisting of gluconic acid, sodium salts of gluconic acid, iminodisuccinic acid, sodium salts of iminodisuccinic acid, and any mixtures thereof.

8. The formulation according to claim 1 wherein said at least one chelating agent is tetrasodium 3-hydroxy-2,2'-iminodisuccinate.

9. The formulation according to claim 1 incorporated into a personal hygiene product to form a preserved personal hygiene product, said formulation being present in a concentration range from about 0.1 to about 10 wt./wt. % of the preserved personal hygiene product.

10. The preserved personal hygiene product according to claim 9 wherein a final pH of the preserved personal hygiene product is in a range from about pH 3 to about pH 9.

11. The preserved personal hygiene product according to claim 9 wherein a final pH of the preserved personal hygiene product is in a range from about pH 5 to about pH 8.

12. The formulation according to claim 1 wherein said at least one alcohol is a combination of phenyl hexanol and nerolidol, and wherein said at least one chelating agent is sodium iminodisuccinate.

13. The formulation according to claim 12 wherein said sodium iminodisuccinate is present in a range from about 3.0% wt./wt. to about 11% wt./wt., and wherein said phenyl hexanol is present in a range from about 20% wt./wt. to about 30% wt./wt., and wherein said nerolidol is present in a range from about 3% wt./wt. to about 7% wt./wt., and wherein said glyceryl laurate is present in a range from about 55% wt./wt. to about 70% wt./wt.

14. The formulation according to claim 1 wherein said at least one alcohol is nerolidol, wherein said at least one chelating agent is sodium iminodisuccinate.

15. The formulation according to claim 14 wherein said sodium iminodisuccinate is present in a range from about 4.0% wt./wt. to about 16% wt./wt., and wherein said nerolidol is present in a range from about 4% wt./wt. to about 11% wt./wt., and wherein said glyceryl laurate is present in a range from about 80% wt./wt. to about 87% wt./wt.

16. The formulation according to claim 1 wherein said at least one chelating agent is tetrasodium 3-hydroxy-2,2'-iminodisuccinate.

17. The formulation according to claim 16 including at least one fatty acid.

18. A preservative formulation for a personal hygiene product, comprising constituents including:
   a) glyceryl laurate present in a concentration from about 55 wt./wt. % to about 87 wt./wt. % of the formulation;
   b) at least one alcohol selected from a group consisting of nerolidol, phenyl hexanol, and any combination thereof, wherein if present, nerolidol is present in a concentration of from about 3 to about 11 wt./wt. %, and wherein if present, phenyl hexanol is present in a concentration of from about 20 to about 30 wt./wt. %; and c) at least one chelating agent present in a concentration from about 0.01 to about 20 wt./wt. % of the formulation; and wherein d) the preservative formulation of constituent a), b) and c) being incorporated into the personal hygiene product to form a preserved personal hygiene product, with the preservative formulation being present in a concentration range from about 0.1 to about 10 wt./wt. % of the preserved personal hygiene product.

19. The formulation according to claim 18 including at least one fatty acid being one of $C_8$ to $C_{22}$ alkyl fatty acids, $C_8$ to $C_{22}$ aryl fatty acids, and any combination thereof.

20. The formulation according to claim 18 including at least one fatty acid being one of $C_{10}$ to $C_{12}$ alkyl fatty acids, $C_{10}$ to $C_{12}$ aryl fatty acids, and any combination thereof.

21. The formulation according to claim 18 wherein said at least one alcohol is phenyl hexanol.

22. The formulation according to claim 18 wherein said at least one alcohol is nerolidol (3,7,11-trimethyl-1,6,10-dodecatrien-3-ol).

23. The formulation according to claim 18 wherein said at least one chelating agent is selected from the group consisting of gluconic acid, sodium salts of gluconic acid, iminodisuccinic acid, sodium salts of iminodisuccinic acid, and any mixtures thereof.

24. The formulation according to claim 18 wherein said at least one chelating agent is tetrasodium 3-hydroxy-2,2'-iminodisuccinate.

25. The formulation according to claim 18 wherein a final pH of the preserved personal hygiene product is in a range from about pH 3 to about pH 9.

26. The formulation according to claim 18 wherein a final pH of the preserved personal hygiene product is in a range from about pH 5 to about pH 8.

27. The formulation according to claim 1 incorporated into a personal hygiene product to form a preserved personal hygiene product, said formulation being present in a concentration range from about 0.1 to about 10 wt./wt. % of the preserved personal hygiene product.

28. The formulation according to claim 27 wherein a final pH of the preserved personal hygiene product is in a range from about pH 3 to about pH 9.

29. The formulation according to claim 18 wherein a final pH of the preserved personal hygiene product is in a range from about pH 5 to about pH 8.

30. The formulation according to claim 17 wherein the fatty acid is lauric acid.

31. The formulation according to claim 18 further including a fatty acid.

32. The formulation according to claim 31 wherein the fatty acid is lauric acid.

* * * * *